United States Patent
Wilmet et al.

(10) Patent No.: US 7,468,467 B2
(45) Date of Patent: Dec. 23, 2008

(54) PROCESS FOR OBTAINING A PURIFIED HYDROFLUOROALKANE

(75) Inventors: Vincent Wilmet, Wavre (BE); Francine Janssens, Vilvoorde (BE); Lionel Casaubon Seignour, Tavaux (FR); Philippe Krafft, Rhode Saint Genese (BE); Alain Lambert, Beauvechain (BE); Olivier Buyle, Autre-Eglise (BE)

(73) Assignee: Solvay S.A. (BE)

( * ) Notice: Subject to any disclaimer, the term of this patent is extended or adjusted under 35 U.S.C. 154(b) by 0 days.

(21) Appl. No.: 11/649,383

(22) Filed: Jan. 3, 2007

(65) Prior Publication Data

US 2007/0112231 A1 May 17, 2007

Related U.S. Application Data

(62) Division of application No. 10/344,037, filed as application No. PCT/EP01/10064 on Aug. 10, 2001, now Pat. No. 7,179,949.

(30) Foreign Application Priority Data

| Aug. 10, 2000 | (FR) | 00 10546 |
| Aug. 10, 2000 | (FR) | 00 10547 |
| Aug. 10, 2000 | (FR) | 00 10548 |
| Aug. 10, 2000 | (FR) | 00 10549 |
| Mar. 7, 2001 | (FR) | 01 03193 |
| Jul. 4, 2001 | (FR) | 01 08910 |

(51) Int. Cl.
C07C 17/00 (2006.01)
C07C 17/10 (2006.01)

(52) U.S. Cl. ...................... 570/165; 570/178

(58) Field of Classification Search ................ 570/170, 570/171, 178, 165
See application file for complete search history.

(56) References Cited

U.S. PATENT DOCUMENTS

| 2,999,885 A | 9/1961 | Heberling, Jr. | |
| 3,101,304 A | 8/1963 | Wiist | |
| 3,218,363 A | 11/1965 | Haseldine | |
| 4,129,603 A * | 12/1978 | Bell | 570/169 |
| 4,801,763 A * | 1/1989 | Maul et al. | 570/177 |
| 4,906,796 A * | 3/1990 | Yates | 571/179 |
| 4,950,364 A | 8/1990 | Wismer | |
| 5,175,380 A * | 12/1992 | Raab | 570/177 |
| 5,233,107 A | 8/1993 | Jansen | |
| 5,475,169 A | 12/1995 | Hopp et al. | |
| 5,510,545 A * | 4/1996 | Jansen | 570/171 |
| 5,616,819 A * | 4/1997 | Boyce et al. | 570/167 |
| 5,621,152 A | 4/1997 | Jansen et al. | |
| 5,785,822 A * | 7/1998 | Cerri et al. | 203/67 |
| 5,801,294 A | 9/1998 | Sage et al. | |
| 5,895,825 A | 4/1999 | Elsheikh et al. | |
| 5,944,962 A | 8/1999 | Boyce | |
| 6,500,994 B1 | 12/2002 | Brosch et al. | |
| 6,858,762 B2 * | 2/2005 | Baker et al. | 570/165 |
| 6,863,780 B2 * | 3/2005 | Nakada et al. | 203/50 |
| 7,094,936 B1 * | 8/2006 | Owens et al. | 570/257 |
| 7,179,949 B2 * | 2/2007 | Wilmet et al. | 570/165 |
| 7,183,448 B2 * | 2/2007 | Nakada et al. | 570/164 |
| 2002/0125122 A1 | 9/2002 | Braun et al. | |

FOREIGN PATENT DOCUMENTS

| CA | 2098245 | 12/1993 |
| CA | 2100594 | 2/1994 |
| CA | 2342925 | 3/2000 |
| DE | 199 40 104 | 3/2000 |
| DE | 100 29 283 | 12/2000 |
| EP | 0 370 688 | 11/1989 |
| EP | 0 511 612 | 4/1992 |
| EP | 0 512 502 | 5/1992 |
| EP | 0 574 756 | 5/1993 |
| EP | 0 582 494 | 6/1993 |
| EP | 0 733 612 | 3/1996 |
| EP | 0 811 591 | 5/1997 |
| EP | 1 132 365 | 11/1999 |
| JP | 04 300 842 | 10/1992 |
| WO | WO-90/08750 | 8/1990 |

(Continued)

OTHER PUBLICATIONS

Yoshinaga, Masami et al, "Purification of hydrochlorofluorocarbons and hydrofluorocarbons" Chemical ABS., 118, No. 19, Abstrract No. 191166, XP-000354050 (May 10, 1993).

*Primary Examiner*—Daniel M Sullian
*Assistant Examiner*—Louisa Lao
(74) *Attorney, Agent, or Firm*—Connolly Bove Lodge & Hutz LLP

(57) ABSTRACT

Process for obtaining a hydrofluoroalkane which is purified of organic impurities, according to which the hydrofluoroalkane containing organic impurities is subjected to at least one purification treatment chosen from (a) a treatment with chlorine in the presence of a initiator
(b) a reaction with hydrogen fluoride
(c) a distillation in which the purified hydrofluoroalkane is removed from the top of the distillation column or from the side
(d) an extractive distillation
(e) an adsorption onto a solid adsorbent
(f) a reaction with a compound containing oxygen, and
(g) a reaction with a compound containing oxygen and a gas-phase reaction with a reagent capable of reacting with at least some of the organic impurities, with the exception of a reaction with elemental chlorine.

20 Claims, No Drawings

FOREIGN PATENT DOCUMENTS

| | | |
|---|---|---|
| WO | WO-97/37955 | 10/1997 |
| WO | WO-98/00381 | 1/1998 |
| WO | WO-00/14040 | 3/2000 |
| WO | WO-00/29361 | 5/2000 |
| WO | WO-01/83411 | 11/2001 |

* cited by examiner

PROCESS FOR OBTAINING A PURIFIED HYDROFLUOROALKANE

CROSS-REFERENCE TO RELATED APPLICATION

The present application is a division of application Ser. No. 10/344,037, filed May 12, 2003, which is a national stage application (under 35 U.S.C. 371) of PCT/EP01/10064 filed Aug. 10, 2001 which claims benefit to French application 00/10549 filed Aug. 10, 2000; French application 00/10548 filed Aug. 10, 2000; French application 00/10547 filed Aug. 10, 2000; French application 00/10546 filed Aug. 10, 2000; French application 01/03193 filed Mar. 7, 2001; and French application 01/08910 filed Jul. 4,2001.

The present invention relates to a process for obtaining a purified hydrofluoroalkane chosen in particular from 1,1,1,3,3-pentafluoropropane and 1,1,1,3,3-pentafluorobutane.

Hydrofluoroalkanes such as 1,1,1,3,3-Pentafluoropropane and 1,1,1,3,3-pentafluorobutane may be used as replacements for (hydro)chlorofluoroalkanes, for example as blowing agents, as refrigerants or as solvents.

These hydrofluoroalkanes are typically manufactured by reacting a chloro or chlorofluoro precursor with hydrogen fluoride. The crude hydrofluoroalkanes obtained in this reaction often contain impurities such as unconverted reagents; hydrogen chloride and olefinic impurities, in particular chlorofluoro olefins containing 3 or 4 carbon atoms.

Patent application WO-A-00/14040 describes a process for purifying 1,1,1,3,3-pentafluorobutane. According to this known process, it is possible to reduce the fluorotrichloroethylene content in 1,1,1,3,3-pentafluorobutane by ionic chlorination in the presence of $FeCl_3$, by hydrogenation in the presence of Pd/Rh on active charcoal or, in particular, by reaction with fluorine.

Patent application WO-A-97/37955 describes a process for purifying 1,1,1,3,3-pentafluoropropane of 1-chloro-3,3,3-trifluoropropene, in which a photochlorination initiated with UV light of wavelength from 300 to 400 nm is carried out The Applicant has now found that hydrofluoroalkenes—that is to say olefins consisting solely of carbon, hydrogen and fluorine—are particularly difficult to remove when they are present as impurity in a hydrofluoroalkane, in particular those comprising from 3 to 5 carbon atoms, most particularly those corresponding to the empirical formula $C_4H_4F_4$, present as impurity in particular in 1,1,1,3,3-pentafluorobutane. On account of the very low chemical reactivity observed, the removal by means of a chemical treatment of the hydrofluoroalkenes in hydrofluoroalkanes is liable to require prolonged treatment times that are undesirable in an industrial process for manufacturing hydrofluoroalkane. In an extreme case, it would not be possible to go below a certain hydrofluoroalkene content.

None of the prior art documents addresses this specific problem.

It was consequently desirable to have available a process for purifying hydrofluoroalkane, in particular 1,1,1,3,3-pentafluoropropane or 1,1,1,3,3-pentafluorobutane, which allows an effective reduction of the content of olefinic impurities and in particular of hydrofluoroalkenes while at the same time using technical means that are simple to implement.

The invention consequently relates to a process for obtaining a hydrofluoroalkane comprising at least three carbon atoms, which is purified of organic impurities, according to which the hydrofluoroalkane containing organic impurities including (chloro)fluoro olefins is subjected to at least one purification treatment chosen from (a) a treatment with chlorine in the presence of an initiator
(b) a reaction with hydrogen fluoride
(c) a distillation in which the purified hydrofluoroalkane is removed from the top of the distillation column or from the side
(d) an extractive distillation
(e) an adsorption onto a solid adsorbent
(f) a reaction with a compound containing oxygen, and
(g) a gas-phase reaction with a reagent capable of reacting with at least some of the organic impurities, with the exception of a reaction with elemental chlorine.

The process according to the invention applies in particular to hydrofluoroalkanes such as 1,1,1,3,3,3-hexafluoropropane (HFC-236fa), 1,1,1,2,3,3,3-heptafluoropropane (HFC-227ea) and 1,1,1,2,3,4,4,5,5,5-decafluoropentane (HFC-43-10mee). Preferably, the hydrofluoroalkane comprises 3 or 4 carbon atoms. The process has been found to be particularly effective for purifying 1,1,1,3,3-pentafluoropropane or 1,1,1,3,3-pentafluorobutane, and most particularly the latter.

It has been found surprisingly that the process according to the invention allows an effective reduction of the content of organic impurities in the hydrofluoroalkane. In particular, 1,1,1,3,3-pentafluorobutane and 1,1,1,3,3-pentafluoropropane have physical and chemical stability under the conditions of the process according to the invention. The process according to the invention may be carried out easily.

The organic impurities whose content may be reduced by means of the process according to the invention generally comprise 3 or 4 carbon atoms. They may also comprise at least one chlorine atom, such as chlorodifluoropropanes and chlorofluorobutanes or -butenes. They are in particular (chloro)fluoro olefins containing 3 or 4 carbon atoms, such as monochlorotrifluorobutene isomers.

The process according to the invention is particularly suitable for effectively removing hydrofluoroalkenes as described above. The process according to the invention, which may be carried out easily, allows an effective reduction of the content of olefinic impurities present in 1,1,1,3,3-pentafluoropropane or 1,1,1,3,3-pentafluorobutane.

In a first aspect of the process according to the invention, the hydrofluoroalkane containing olefinic impurities, in particular hydrofluoroalkenes comprising from 3 to 5 carbon atoms, is subjected to a treatment with chlorine in the presence of an initiator.

The treatment with chlorine serves to chlorinate the olefinic impurities in the hydrofluoroalkane containing olefinic impurities. These are notably (chloro)fluoro olefins containing 3 or 4 carbon atoms or, in particular, the hydrofluoroalkenes mentioned above.

The initiator serves to decompose the chlorine molecules by cleavage. In a first variant of the first aspect of the process according to the invention, the the initiator is a free-radical initiator selected from an organic or inorganic initiator compound.

To promote the mixing of the hydrofluoroalkane containing olefinic impurities with the initiator compound, the first variant of the first aspect of the process according to the invention is preferably carried out in the liquid phase.

According to the invention, the free-radical initiator is often an organic compound. Among the organic compounds that are usually used are peroxide or diazo compounds. Peroxide compounds are used in particular. Among these, the ones chosen more particularly are diacyl peroxides, peroxydicarbonates, alkyl peresters, peracetals, ketone peroxides, alkyl hydroperoxides and dialkyl peroxides. Diacyl peroxides or peroxydicarbonates are preferably selected. Excellent results have been obtained with dilauroyl peroxide, dibenzoyl peroxide or dicetyl peroxydicarbonate.

The free-radical initiator may also be an inorganic compound. In this case, it is often chosen from hydrogen peroxide, percarbonates such as, in particular, sodium percarbonate, and perborates such as sodium perborate.

The initiator compound is preferably selected from compounds with a half-life from 0.1 to 3 hours and usually of about 1 hour at the temperature of the treatment with chlorine.

The initiator compound is generally used in a proportion of at least about 10 ppm by weight relative to the hydrofluoroalkane containing olefinic impurities. At least about 20 ppm by weight of initiator compound are used. Even more particularly at least about 30 ppm by weight in particular. Most frequently, not more than about 10 000 ppm by weight of initiator compound are used relative to the hydrofluoroalkane containing olefinic impurities. Preferably, the amount of organic initiator compound does not exceed about 1 000 ppm by weight and even more preferably it does not exceed about 300 ppm by weight.

In the first variant of the first aspect of the process according to the invention, the chlorine may be used in the gas phase or in the liquid phase. It is introduced in excess amounts relative to all of the olefinic impurities to be chlorinated in the hydrofluoroalkane containing olefinic impurities. Generally, the chlorine is used in a proportion of more than 3 mol per mole of olefinic impurities and preferably at least about 4 mol per mole of olefinic impurities. Generally, it is not desirable to exceed about 40 mol of chlorine per mole of olefinic impurities. It is preferable to limit the amount used so that virtually all of the chlorine can react and is not found in unchanged form after the present purification treatment. Preferably, the amount does not exceed about 15 mol per mole of olefinic impurities and even more preferably this ratio does not exceed about 12.

In the first variant of the first aspect of the process according to the invention, the treatment with chlorine may be carried out over a wide temperature range. In particular, the treatment with chlorine is carried out at a temperature of at least about 40° C. and even more particularly of at least about 60° C. Higher temperatures allow a faster conversion of the unsaturated compounds. However, this results in a correlative increase in pressure, of which account needs to be taken. Preferably, the treatment temperature does not exceed about 150° C. and even more preferably it does not exceed about 100° C. Excellent results have been obtained when the treatment with chlorine is carried out in the regions of 60 to 100° C.

In the first variant of the first aspect of the process according to the invention, the treatment with chlorine may be carried out at the autogenous pressure or a higher pressure generated, for example, by introducing an inert gas. In general, the treatment is carried out at a pressure which does not exceed about 5 MPa and preferably 2 MPa Pressures from about 0.2 to about 1.0 MPa are suitable for use.

These correlated conditions of high temperature and high pressure which are allowed for the treatment with chlorine contribute towards the fast and effective removal of the olefinic impurities. In the first variant of the first aspect of the process according to the invention, the duration of the treatment with chlorine may be from about 1 to about 120 minutes. Preferably, the duration of the treatment with chlorine is not more than about 60 minutes.

According to an advantageous embodiment of the first variant of the first aspect of the process according to the invention, the initiator compound is introduced into the hydrofluoroalkane containing olefinic impurities before the chlorine. In a preferred implementation variant of this embodiment of the invention, the chlorine is introduced into the hydrofluoroalkane at a temperature close to the treatment temperature. In a particularly preferred implementation variant of this embodiment of the invention, the initiator compound is also introduced into the hydrofluoroalkane at a temperature close to the treatment temperature.

In a second variant of the first aspect of the process according to the invention, the initiator, which is a free-radical initiator, is an electromagnetic radiation comprising at least one fraction of wavelengths less than 280 nm.

It has been found, surprisingly, that this variant of the first aspect of the process according to the invention is particularly effective for reducing to an acceptable level the amount of the hydrofluoroalkenes which may be contained in a hydrofluoroalkane, quickly and without substantial degradation of the hydrofluoroalkane. This variant of the first aspect of the process according to the invention allows the chlorine to be used in the presence of a broader spectrum of wavelengths than in the known processes. This variant of the first aspect of the process according to the invention allows an accelerated purification operation, an efficient destruction of the chlorine-free impurities and an improved use of energy.

This variant of the first aspect of the process according to the invention is particularly suitable for purifying 1,1,1,3,3-pentafluorobutane of hydrofluoroalkenes. It is more particularly suitable for purifying 1,1,1,3,3-pentafluorobutane of hydrofluoroalkenes of empirical formula $C_4H_4F_4$, in particular E-CF3—CH=CF—CH3, Z-CF3—CH=CF—CH3, E-CF3—CH=CH—CH2F, Z-CF3—CH=CH—CH2F, E-CF3—CH2—CH=CHF, Z-CH3—CH2—CH=CHF and/or CF3—CH2—CF=CH2. The process is particularly suitable for purifying 1,1,1,3,3-pentafluorobutane of one or more hydrofluoroalkenes chosen from E-CF3-CH=CF—CH3, Z-CF3—CH=CF—CH3 and CF3—CH2—CF=CH2.

It is understood that the first variant of the first aspect of the process according to the invention and any of the methods described below may also be used to purify the hydrofluoroalkane, in particular 1,1,1,3,3-pentafluorobutane, of hydrofluoroalkenes as mentioned above. However, the second variant of the first aspect of the process according to the invention is, in the light of the advantages described above, most particularly preferred for purifying hydrofluoroalkanes of hydrofluoroalkenes.

In the second variant of the first aspect of the process according to the invention, the energy of the fraction of wavelengths less than 280 nm is generally at least 5% of the total energy of the electromagnetic radiation. Preferably, the energy of the fraction of wavelengths less than 280 nm is at least 10% of the total energy of the electromagnetic radiation. An electromagnetic radiation in which 100% of the energy is contained in the fraction of wavelengths less than 280 nm may even be used.

The wavelengths in the fraction of wavelengths less than 280 nm are preferably essentially at least 170 nm. In a more particularly preferred manner, the wavelengths are essentially at least 180 nm. In one variant, the fraction of wavelengths comprises radiation of wavelength less than or equal to 270 nm, in particular 260 nm.

Sources of electromagnetic radiation comprising a fraction of wavelengths less than 280 nm are, for example, ultraviolet (UV) burners such as, in particular, medium pressure or, preferably, low pressure, optionally doped, high power mercury vapour burners. Such burners are commercially available, for example from companies Hereaus or ABB. A monochromatic burner of suitable wavelength may also be used.

The separation between the burner and the reaction medium in which the purification reaction is carried out is generally achieved with a translucent material which allows electromagnetic radiation of wavelength less than 280 nm to pass through. An example of such a material is quartz.

The intensity of the electromagnetic radiation is generally at least 0.01 W.h per kg of hydrofluoroalkane containing impurities, preferably at least 0.02 $W.h.kg^{-1}$ or even at least 0.05 $W.h.kg^{-1}$. The intensity of the electromagnetic radiation is generally not more than 5 W.h per kg of hydrofluoroalkane containing impurities and preferably not more than 3 $W.h.kg^{-1}$ or even not more than 2 $W.h.kg^{-1}$.

In the second variant of the first aspect of the process according to the invention, the chlorine may be used in the gas phase or in the liquid phase. It is preferably used in the liquid phase.

The second variant of the first aspect of the process according to the invention may be carried out, for example, in a falling film photoreactor or in an immersed burner photoreactor.

In a first embodiment of the second variant of the first aspect of the process according to the invention, the chlorine is introduced in stoichiometric or excess amounts relative to the entirety of the olefinic impurities to be chlorinated in the hydrofluoroalkane containing impurities. In this embodiment, the chlorine is used in an amount of greater than or equal to about 1 mol per mole of olefinic impurities. The amount of chlorine is, in this embodiment, generally less than or equal to about 10 mol of chlorine per mole of olefinic impurities. Preferably, the amount does not exceed about 5 mol of chlorine per mole of olefinic impurities and even more preferably this ratio does not exceed about 2.

In a second embodiment of the second variant of the first aspect of the process according to the invention, the chlorine is introduced in amounts less than the entirety of the olefinic impurities to be chlorinated in the hydrofluoroalkane containing impurities. In this variant, the chlorine is preferably used in an amount of less than about 0.9 mol per mole of olefinic impurities. The amount of chlorine is, in this embodiment, generally greater than or equal to about 0.01 mol of chlorine per mole of olefinic impurities. Preferably, this amount is greater than or equal to about 0.1 mol of chlorine per mole of olefinic impurities. An amount of greater than or equal to about 0.5 mol of chlorine per mole of olefinic impurities is most particularly preferred.

In the second variant of the first aspect of the process according to the invention, the treatment with chlorine is generally carried out at a temperature of greater than or equal to −20° C. The temperature is often greater than or equal to 0° C. Preferably, the temperature is greater than or equal to about 10° C. In this variant, the treatment with chlorine is generally carried out at a temperature of less than or equal to 150° C. The temperature is often less than or equal to 100° C. Preferably, the temperature is less than or equal to about 60° C.

In the second variant of the first aspect of the process according to the invention, the pressure at which the treatment with chlorine is carried out is generally greater than or equal to about 1 bar. The pressure at which the treatment with chlorine is carried out is generally less than or equal to about 10 bar. Preferably, the pressure is less than or equal to about 5 bar.

In the second variant of the first aspect of the process according to the invention, the duration of the treatment with chlorine is generally greater than or equal to 5 min. The duration of the treatment with chlorine is often greater than or equal to 10 min. Preferably, the duration of the treatment with chlorine is greater than or equal to 15 min. In the second variant of the first aspect of the process according to the invention, the duration of the treatment with chlorine is generally less than or equal to 10 h. The duration of the treatment with chlorine is often less than or equal to 5 h. Preferably, the duration of the treatment with chlorine is less than or equal to about 3 h. In a particularly preferred manner, it does not exceed 2 h.

In a third variant of the first aspect of the invention the initiator is a low amount of metal ion. The third variant is carried out preferably in the substantial absence of free-radical initiators. In particular it is preferably carried out in the substantial absence of electromagnetic radiation having a wavelength from 170 nm to 400 nm (UV-light). According to this variant, efficient elimination of hydrofluoroalkenes such as mentioned above may be achieved, without substantial degradation of the desired hydrofluoroalkane. In this variant, no specific separation operation is required to separate the iniator from the hydrofluoroalkane. Alternatively, the initiator is separated easily by an optional distillation The metal ion is preferably a lewis acid. It is preferably selected from ions of group IIIa, IVa and b, Va and b, VIb and VIII metals of the Periodic Table of Elements (IUPAC 1970). In a particularly suitable manner, it is selected from ions of iron, nickel, aluminium, boron, titanium, chromium, zirconium, tantalum, tin or antimony. Iron ions are particularly preferred.

The amount of metal ion present in the treatment with chlorine is generally at most 1000 ppm by weight relative to the hydrofluoroalkane containing organic impurities. The amount of metal ion is more frequently at most 100 ppm. The amount is preferably at most 50 ppm. An amount of metal ions of at most 30 ppm is particularly preferred. The amount of metal ion present in the treatment with chlorine is generally at least 0.01 ppm by weight relative to the hydrofluoroalkane containing organic impurities. The amount of metal ion is more frequently at least 0.1 ppm. The amount is preferably at least 0.5 ppm.

The metal ion can be introduced into the reaction medium for example by addition of a suitable metal compound. In a particular embodiment, the treatment with chlorine is carried out in a reactor made of a material containing a suitable metal as described above, under conditions sufficient to release at least a trace amount of metal ion.

In the third variant of the first aspect of the process according to the invention, the treatment with chlorine is generally carried out at a temperature of greater than or equal to 0° C. The temperature is often greater than or equal to 20° C. Preferably, the temperature is greater than or equal to about 40° C. In this variant, the treatment with chlorine is generally carried out at a temperature of less than or equal to 200° C. The temperature is often less than or equal to 150° C. Preferably, the temperature is less than or equal to about 100° C.

In the third variant of the first aspect of the process according to the invention, the duration of the treatment with chlorine is generally greater than or equal to 1 h. The duration of the treatment with chlorine is often greater than or equal to 3 h In the third variant of the first aspect of the process according to the invention, the duration of the treatment with chlorine is generally less than or equal to 20 h Preferably, the duration of the treatment with chlorine is less than or equal to about 10 h.

The suitable pressures in the third variant of the first aspect of the process according to the invention, are the same as in the second variant of the first aspect of the process according to the invention.

In the third variant of the first aspect of the process according to the invention, the hydrofluoroalkane is suitably selected from the group consisting of 1,1,1,2,3,3,3-heptafluoropropane, 1,1,1,3,3,3-hexafluoropropane, 1,1,1,3,3-pentafluoropropane and 1,1,1,3,3-pentafluorobutane. It is preferably selected from 1,1,1,3,3-pentafluoropropane and 1,1,1,3,3-pentafluorobutane. Most preferably, the hydrofluoroalkane is 1,1,1,3,3-pentafluorobutane.

In another embodiment, the third variant of the first aspect of the process according to the invention can also advantageously be used for the chlorination of bulk chloro(fluoro) olefins such as described above or of fractions comprising a high amount of such chloro(fluoro)olefins.

The first aspect of the process according to the invention may be carried out in batchwise, semi-continuous or continuous mode. A continuous mode is preferred.

In the first aspect of the process according to the invention, the chlorination reactor and the distillation apparatus are preferably made of corrosion-resistant materials such as, in particular, alloys of the type such as MONEL, INCONEL or HASTELLOY.

In the first aspect of the process according to the invention, care is advantageously taken to ensure that the oxygen content in the chlorine is less than 1000 ppm by volume and preferably that it does not exceed 50 ppm by volume. To do this, the hydrofluoroalkane containing olefinic impurities may first be deaerated by sparging with an inert gas, for example nitrogen.

In the first aspect of the process according to the invention, the treatment with chlorine is generally followed by a separation operation whose function is to separate the impurities from the hydrofluoroalkane, after they have been chlorinated. The separation operation is preferably a distillation.

The first aspect of the process according to the invention applies in a most particularly preferred manner to the production of purified 1,1,1,3,3-pentafluorobutane.

In a second aspect of the process according to the invention, the hydrofluoroalkane containing organic impurities is subjected to a reaction with hydrogen fluoride.

The second aspect makes it possible in particular to effectively reduce the content of organic impurities present in the hydrofluoroalkane by using hydrogen fluoride. The latter compound is among reagents used in a synthesis of a hydrofluoroalkane by hydrofluorination. The products of the conversion are saturated (hydro)fluoroalkanes which are toxicologically and environmentally more acceptable than olefinic or chlorofluoro organic impurities. In addition, for certain organic impurities, the reaction with hydrogen fluoride will lead to the formation of the desired hydrofluoroalkane, namely, in particular, 1,1,1,3,3-pentafluoropropane or 1,1,1,3,3-pentafluorobutane. The second aspect of the process according to the invention may be carried out readily by using technical means developed for reactions for the synthesis of hydrofluoroalkanes by hydrofluorination.

The organic impurities whose content may be reduced in particular in the second aspect of the process according to the invention comprise at least one chlorine atom, such as chlorodifluoropropanes and chlorofluorobutanes or -butenes. They are in particular (chloro)fluoro olefins containing 3 or 4 carbon atoms, such as monochlorotrifluorobutene isomers.

The second aspect of the process according to the invention is also particularly useful for the elimination of the hydrofluoroalkenes mentioned above.

In the second aspect of the process according to the invention, the reaction of the hydrofluoroalkane with hydrogen fluoride is preferably carried out in the presence of a fluorination catalyst. It may also be carried out in the absence of catalyst.

When the reaction of the hydrofluoroalkane with hydrogen fluoride is carried out in the presence of a catalyst, catalysts which can promote the addition of HF to an olefin and/or the replacement of a chlorine atom with a fluorine atom may be used. Among the catalysts which may be used, mention may be made of derivatives of metals chosen from the metals from groups IIIa, IVa and b, Va and b and VIb of the Periodic Table of the Elements (IUPAC, 1970) and mixtures thereof. Titanium, tantalum, molybdenum, boron, tin and antimony derivatives are more especially selected. Preferably, titanium or tin derivatives are used. Metal derivatives which may be mentioned are salts and more particularly halides. Preferably, the choice is made from chlorides, fluorides and chlorofluorides. Catalysts that are particularly preferred in the process for preparing the hydrofluoroalkane according to the invention are the chlorides, fluorides and chlorofluorides of titanium and of tin and mixtures thereof. Titanium tetrachloride and tin tetrachloride are particularly suitable for use.

In the second aspect of the process according to the invention, the molar ratio between the hydrogen fluoride and the organic impurities present in the hydrofluoroalkane is generally at least 1 mol/mol. Preferably, the process is performed with a molar ratio of at least 1.5 mol/mol. The molar ratio between the hydrogen fluoride and the organic compound used generally does not exceed 1000 mol/mol. It is preferable for this molar ratio not to exceed 10 mol/mol. In the second aspect of the process according to the invention, a molar ratio between the hydrogen fluoride and the olefinic impurities of not more than 3 is often maintained.

The second aspect of the process according to the invention may be carried out in batchwise or continuous mode.

When the second aspect of the process according to the invention is carried out in batchwise mode, the duration of the reaction of the hydrofluoroalkane containing organic impurities with hydrogen fluoride generally ranges from 10 min to 5 h. Preferably, this duration is at least 0.5 h. Advantageously, this duration is at least 1 h. In general, this duration does not exceed 4 h. Preferably, this duration does not exceed 2.5 h.

When the second aspect of the process according to the invention is carried out in continuous mode, the residence time of the reagents in the reactor is generally at least 0.5 h. Usually it does not exceed 30 h. Typically it ranges from 5 to 25 h. Preferably, it ranges from 10 to 20 h. The expression "residence time of the reagents in the factor" is intended to denote the ratio between the volume of the reaction medium and the flow rate by volume of the reaction medium at the reactor outlet.

In a first variant, which is preferred, the reaction of the hydrofluoroalkane containing organic impurities with hydrogen fluoride in the second aspect of the process according to the invention is carried out in the liquid phase. In this variant, the temperature at which the reaction of the hydrofluoroalkane containing organic impurities with hydrogen fluoride is carried out is generally at least 60° C. Preferably, the temperature is at least 80° C. In general, the temperature does not exceed 160° C. Preferably, it does not exceed 140° C.

In this variant, the pressure is chosen so as to keep the reaction medium in liquid form. The pressure used varies as a function of the temperature of the reaction medium. It is generally less than or equal to 40 bar. Preferably, it is less than or equal to 35 bar. In a particularly advantageous manner, the pressure is less than or equal to 25 bar. In general, the pressure is greater than or equal to 5 bar. Preferably, the pressure is greater than or equal to 10 bar.

In a second variant, the second aspect of the process according to the invention is carried out in the gas phase. This variant is particularly suitable for purifying 1,1,1,3,3-pentafluoropropane and 1,1,1,3,3-pentafluorobutane.

Specifically, 1,1,1,3,3-pentafluoropropane and 1,1,1,3,3-pentafluorobutane, and in particular 1,1,1,3,3-pentafluorobutane, show surprising thermal stability, which allows them to be purified in the gas phase.

In this second variant, a fluorination catalyst based on a metal oxide chosen from chromium oxide, zirconium oxide and aluminium oxide, and mixtures thereof, is often used. Often, the metal oxide has a specific surface area determined according to the BET method of at least 100 $m^2/g$ and preferably of at least 150 $m^2/g$. Generally, this specific surface area is not more than 400 $m^2/g$. The metal oxide is preferably amorphous.

In this second variant, the temperature of the reaction with hydrogen fluoride is generally at least 50° C. Preferably, the temperature is at least 100° C. Generally, the temperature is not more than 400° C. Preferably, the temperature is not more than 300° C.

The second aspect of the process according to the invention finds an advantageous application to the purification of a hydrofluoroalkane obtained by synthesis by hydrofluorination, in particular by hydrofluorination of a chloro(fluoro) carbon. In the latter case, it may be advantageous to reduce the hydrogen chloride content of the hydrofluoroalkane containing organic impurities prior to its use in the second aspect of the process according to the invention.

The second aspect of the process according to the invention often comprises at least one subsequent treatment step intended to recover the hydrofluoroalkane. Examples of treatment steps which may be used are, inter alia, treatments which may be used to separate the residual hydrogen fluoride from the hydrofluoroalkane, such as, for example, adsorption onto a solid, for instance NaF or alumina, washing with water, an extraction operation, a separation by means of a suitable membrane, an extractive distillation or a distillation.

In a third aspect of the invention, the hydrofluoroalkane containing organic impurities is subjected to a distillation and the purified hydrofluoroalkane is removed from the top of the distillation column or from the side.

It has been found, surprisingly, that organic impurities present in the hydrofluoroalkane, in particular (hydro)(chloro)fluorocarbons comprising 3 or 4 carbon atoms, do not have a tendency to form an azeotrope with the hydrofluoroalkane and can thus be separated by means of the third aspect of the process according to the invention. The third aspect of the process according to the invention may be carried out easily.

The organic impurities whose content may be reduced by the third aspect of the process according to the invention generally comprise 3 or 4 carbon atoms. They are in particular hydrochlorofluoroalkanes and (chloro)fluoro olefins containing 3 or 4 carbon atoms, such as monochlorotrifluorobutene isomers. The third aspect of the process according to the invention is also particularly useful for the elimination of the hydrofluoroalkenes mentioned above.

The distillation pressure is generally less than 10 bar absolute. It is usually not more than 5 bar. Preferably, it is not more than 3 bar. Generally, the distillation pressure is at least 0.5 bar. It is usually at least 1 bar. Preferably, it is at least 1.5 bar.

In the present description of the third aspect of the process according to the invention, any reference to the pressure corresponds to the absolute pressure measured at the top of the distillation column.

The temperature at which the distillation is carried out corresponds approximately to the boiling point of the hydrofluoroalkane at the chosen pressure.

When the hydrofluoroalkane is 1,1,1,3,3-pentafluorobutane, good results are obtained at a pressure of about 1.5 to 3 bar and a temperature of about 50 to 70° C.

The distillation may be carried out in one or more distillation columns. Preferably, only one column will be used.

The distillation columns which may be used are known per se. It is possible to use, for example, conventional plate columns or "dual-flow" plate columns or columns with bulk or structured packing.

The number of theoretical plates in the distillation is generally at least 10. It is usually at least 15. A number of at least 20 gives good results.

The feed of hydrofluoroalkane containing organic impurities in the third aspect of the process according to the invention is generally carried out at a level below 50% of the number of theoretical plates of the column, it being understood that the top of the column corresponds to 100% of the number of theoretical plates. This level is usually not more than 45% of the number of theoretical plates of the column. Generally, the feed is carried out at a level of at least 5% of the number of theoretical plates of the column. This level is usually at least 10% of the number of theoretical plates of the column.

If a side removal is carried out, it is generally carried out at the level which corresponds to at least 50% of the number of theoretical plates of the distillation. The side removal is generally carried out at the level which corresponds to not more than 80% of the number of theoretical plates of the distillation.

In the third aspect of the process according to the invention, the purified hydrofluoroalkane is generally removed in an amount of at least 50% of the feed. The amount is usually at least 70% of the feed. The amount is preferably at least 80% of the feed. Generally, the purified hydrofluoroalkane is removed in an amount of not more than 99% of the feed. The amount is usually not more than 97% of the feed. The amount is preferably not more than 95% of the feed.

The degree of molar reflux in the distillation is generally not more than 20. This degree is usually not more than 10. A degree of reflux of not more than 7 has given good results.

In a fourth aspect of the process according to the invention, the purification treatment is an extractive distillation. The extractive distillation is carried out in the presence of at least one extractant which is generally chosen from (hydro)chlorocarbons, (hydro)fluorocarbons, hydrochlorofluorocarbons, hydrocarbons, ketones, alcohols, ethers, esters, nitriles, hydrogen chloride and carbon dioxide.

Hydrofluorocarbons which may be used as extractants comprise typically from 1 to 6 carbon atoms, preferably from 1 to 4 carbon atoms. Preferred specific hydrofluorocarbon extractants are hydrofluoroalkane extractants chosen, for example, from difluoromethane, 1,1,1,2-etrafluoroethane, 1,1,1-trifluoroethane, pentafluoroethane, 1,1,1,2,3,3,3-heptafluoropropane 1,1,1,3,3-pentafluoropropane and 1,1,1,3,3-pentafluorobutane. It is understood that the hydrofluorocarbon extractant in the fourth aspect of the process according to the invention is, in general, different from the hydrofluoroalkane containing organic impurities.

Other extractants which may be used are chosen, for example, from dichloromethane, perchloroethylene, n-pentane, n-hexane, methanol, ethanol, isopropanol, diethyl ether, acetone, 2-butanone, ethyl acetate and acetonitrile.

In another embodiment, the extractant is chosen from chlorinated precursors suitable for a synthesis of the hydrofluoroalkane by hydrofluorination or from chloro(fluoro) intermediates obtainable by hydrofluorination of a said chlorinated precursor, such as chlorofluoropropanes and chlorofluorobutanes.

Preferably, the extractant is chosen from 1,1,1,3,3-pentachlorobutane, 1,1-dichloro-1,3,3-trifluorobutane, 1,3-dichloro-1,1,3-trifluorobutane, 3,3-dichloro-1,1,1-trifluorobutane, 1-chloro-1,3,3,3-tetrafluorobutane and 3-chloro-1,1,3,3-tetrafluorobutane or a mixture of these extractants.

The distillation is generally carried out at a pressure and a temperature which makes it possible essentially to avoid, where appropriate, the formation of azeotropes between the extractant and the hydrofluoroalkane.

The distillation may be performed in one or more distillation columns. Preferably, only one column will be used.

The distillation columns which may be used in the fourth aspect of the process according to the invention are known per se. It is possible to use, for example, conventional plate columns or "dual-flow" plate columns or columns with bulk or structured packing.

In a fifth aspect of the process according to the invention, the purification treatment is an adsorption onto a solid adsorbent. The solid adsorbent may be chosen, for example, from aluminas, silicas, iron oxide compounds, zeolites and active charcoals. Such adsorbents are commercially available. The adsorbent is optionally activated prior to its use in the adsorption treatment. A heat treatment or a treatment intended to increase the Lewis acidity of the solid adsorbent is suitable. The preferred solid adsorbents are those which have undergone a treatment intended to increase their Lewis acidity, for example a washing with hydrochloric acid or with nitric acid.

The contact between the hydrofluoroalkane containing organic impurities and the solid adsorbent may be carried out according to various techniques. The process may be performed in a fluidized bed, but it is generally preferred to place the solid adsorbent in the form of a fixed bed of particles, through which is passed a flow of the hydrofluoroalkane containing organic impurities. This flow may be liquid or gaseous. In one variant, the adsorption is carried out in the gas phase.

When the fifth aspect of the process is carried out in the gas phase, a contact time between the hydrofluoroalkane containing organic impurities and the solid adsorbent of at least 1 s is carried out. Preferably, the process is performed with a contact time of greater than 2 s. Good results have been obtained with a contact time of greater than or equal to 3 s. In principle, the process may be performed with a very long contact time, for example of several minutes. In practice, for reasons of efficiency, the process is generally performed with a contact time of less than 1 minute and preferably less than or equal to about 30 s.

When the fifth aspect of the process is carried out in the liquid phase, a contact time between the hydrofluoroalkane containing organic impurities and the solid adsorbent of at least about 2 minutes is carried out. Preferably, the process is performed with a contact time of greater than about 5 minutes.

In principle, the process may be performed with a very long contact time, for example of 120 minutes. In practice, the process is generally performed with a contact time of less than 60 minutes and preferably less than or equal to about 30 minutes.

When the fifth aspect of the process is carried out in a fixed bed, the contact time is defined as the ratio of the volume of the bed of adsorbent to the flow rate by volume of the stream of hydrofluoroalkane containing organic impurities. When the fifth aspect of the process is carried out in a fluidized bed, the contact time is defined as the ratio of the volume of the tank containing the solid adsorbent to the flow rate by volume of the stream of hydrofluoroalkane containing organic impurities.

The solid adsorbent is used in the form of a powder of particles whose optimum particle size depends on the conditions under which the process is carried out. In general, a solid adsorbent whose particle diameter ranges from about 0.1 mm to 10 mm is selected The process is preferably performed with particles with a diameter of less than or equal to 7 mm. In a particularly preferred manner, particles with a diameter of less than or equal to 5 mm are used. Moreover, it is preferred to use a solid adsorbent whose particles have a diameter of greater than or equal to 0.5 mm. The process is preferably performed with particles with a diameter of greater than or equal to 1 mm. In a particularly preferred manner, particles with a diameter of greater than or equal to 2 mm are used.

After the process, the solid adsorbent may be regenerated by heating at moderate temperature, for example 100 to 250° C., under a stream of gas, for example under nitrogen, or under reduced pressure. The solid adsorbent may also be regenerated by a treatment with oxygen.

In a sixth aspect of the process according to the invention, the purification treatment is a reaction with a compound containing oxygen. It has been found that reagents containing oxygen react preferentially with the organic impurities present in the hydrofluoroalkane, in particular in 1,1,1,3,3-pentafluorobutane and essentially without degrading the hydrofluoroalkane, in particular 1,1,1,3,3-pentafluorobutane. The compound containing oxygen may be, for example, an oxygenated gas, an oxygenated acid, an organic or inorganic peroxide, a peroxide salt or a peracid. Specific examples of such compounds are chosen from oxygen, ozone, hydrogen peroxide, peracetic acid, potassium permanganate, sulphuric acid and sulphur trioxide.

In another embodiment of the sixth aspect of the process according to the invention, the reaction is carried out in the presence of a base and the compound containing oxygen is an alcohol. The base may be, for example, an alkali metal hydroxide such as sodium hydroxide or potassium hydroxide. The alcohol may be chosen, for example, from methanol, ethanol and isopropanol.

The reaction with the compound containing oxygen may be carried out in the presence or in the absence of an oxygenation catalyst. Oxygenation catalysts which may be used may be chosen, for example, from compounds and in particular from complexes containing platinum, manganese or titanium.

The reaction with the compound containing oxygen may be carried out in the gas phase or in the liquid phase. It is preferably carried out in the liquid phase. In this case, the reaction temperature is generally not more than 150° C. The temperature is more frequently not more than 120° C. Preferably, the temperature is not more than 100° C. The reaction temperature is generally at least −20° C. The temperature is more frequently at least 0° C. Preferably, the temperature is at least 20° C.

The reaction pressure is generally from 1 to 10 bar.

In a seventh aspect of the process according to the invention, the purification treatment is a reaction in the gas phase with a reagent capable of reacting with at least some of the organic impurities, with the exception of a reaction with elemental chlorine.

In the seventh aspect of the process according to the invention, the reagent may in principle be any reagent capable of reacting in the gas phase with at least some of the organic impurities present in the hydrofluoroalkane and in particular with the olefinic impurities. The reagent is advantageously chosen from hydrogen chloride, hydrogen, hydrogen fluoride, oxygen and ozone.

In a typical example, the reaction is a catalytic hydrogenation.

It has been found, surprisingly, that catalytic hydrogenation makes it possible to reduce the content of any impurity in particular in 1,1,1,3,3-pentafluorobutane to a level close to, even less than, 5 mg/kg, while at the same time avoiding degradation of the hydrofluoroalkane, in particular of 1,1,1,3,3-pentafluorobutane.

Catalysts which may be used in the catalytic hydrogenation reaction in the gas phase according to the invention are, for example, catalysts containing a metal from group VIII of the Periodic Table of Elements (IUPAC, 1970) or a mixture of several metals, preferably supported on a support such as active charcoal, a fluorinated alumina or aluminium trifluoride. Specific examples of metals from group VIII are platinum, palladium and rhodium. Among these catalysts, a catalyst comprising palladium is preferred.

The metal content in the supported catalysts which may be used is generally at least 0.001% by weight This content is usually at least 0.1% by weight. The metal content in the supported catalysts is generally not more than 20% by weight This content is frequently not more than 10% by weight. A catalyst which is resistant with respect to the products which may be present during the catalytic hydrogenation, in particular hydrogen fluoride, is preferably chosen. Good results are obtained, for example, with a catalyst comprising palladium supported on active charcoal.

The molar ratio between the reagent and the organic impurities present in the hydrofluoroalkane is generally at least 1 mol/mol. Preferably, the process is performed with a molar ratio of at least 1.5 mol/mol. The molar ratio between the reagent and the organic impurities generally does not exceed 1000 mol/mol. It is preferable for this molar ratio not to exceed 10 mol/mol. In the seventh aspect of the process according to the invention, a molar ratio between the reagent and the olefinic impurities of not more than 3 is frequently maintained. However, when the reagent is hydrogen, good results are also obtained when a molar ratio between the hydrogen and the olefinic impurities of greater than or equal to 5 is maintained. The molar ratio between the hydrogen and the olefinic impurities is advantageously less than or equal to 20. Preferably, this ratio is less than or equal to 10.

The temperature of the gas-phase reaction is generally at least 50° C. This temperature is usually at least 70° C. Preferably, this temperature is greater than or equal to 100° C. Generally, the temperature of the gas-phase reaction is not more than 400° C. Preferably, this temperature is not more than 300° C. In a particularly preferred manner, this temperature is not more than 250° C. Even more preferably, this temperature is not more than 150° C.

In the seventh aspect of the process according to the invention, it is often necessary to carry out an operation intended to place the hydrofluoroalkane containing the organic impurities into the gaseous form. This operation may comprise, for example, an evaporation. In one preferred variant, the operation comprises the removal, in the gaseous form, of a distillation fraction comprising hydrofluoroalkane and organic impurities, for the purpose of purifying it in the gas phase. The distillation fraction may be obtained by one or more distillations of crude hydrofluoroalkane comprising, in addition to organic impurities, possibly reagents arising as by-products or intermediates of the synthesis of the hydrofluoroalkane. The crude hydrofluoroalkane may in particular comprise hydrogen fluoride and/or hydrogen chloride, in particular when the hydrofluoroalkane is obtained by hydrofluorination. The hydrogen fluoride and/or hydrogen chloride content in the crude hydrofluoroalkane may be reduced by distillation, such that the distillation fraction has a low hydrogen fluoride and/or hydrogen chloride content.

This reduction of the hydrogen fluoride and/or hydrogen chloride content is particularly advantageous when a catalytic hydrogenation as described above is carried out. In this case, hydrofluoroalkane containing organic impurities and having an acidity of not more than 1000 mmol/kg is generally used in the purification treatment. Preferably, the acidity is not more than 100 mmol/kg. Good results are obtained with hydrofluoroalkane containing organic impurities that are essentially free of hydrogen fluoride and/or hydrogen chloride.

In the operation intended to place the hydrofluoroalkane containing the organic impurities into the gaseous form, care is generally taken to ensure that the temperature of the hydrofluoroalkane does not exceed the temperature of the gas-phase purification treatment.

In the seventh aspect of the process according to the invention, the gas-phase purification reaction may be advantageously followed by one or more treatments intended to separate the hydrofluoroalkane from the products of reaction between the organic impurities and the reagent. A distillation is suitable as a treatment, in particular when the reagent is hydrogen.

In the process according to the invention, the purification treatment may be followed by one or more finishing steps intended, for example, to remove any residual acidity, in particular traces of hydrogen fluoride. A suitable finishing step for this purpose is, for example, an adsorption onto a solid such as alumina, NaF or silica.

Other treatments which may be used are, for example, a washing with water, an extraction operation or a separation by means of a suitable membrane.

The process according to the invention applies to the purification of a hydrofluoroalkane containing olefinic impurities, prepared by any synthetic process, without a pretreatment being required. The process according to the invention also applies to the purification of a hydrofluoroalkane containing organic impurities, which consists essentially of hydrofluoroalkane and organic impurities. Typically, the hydrofluoroalkane to be purified contains not more than 10% by weight of organic impurities. This content of impurities may be not more than 5% by weight. It may even be not more than 1% by weight. The process according to the invention may even be applied to a hydrofluoroalkane containing not more than 0.1% by weight of organic impurities.

The process according to the invention finds an advantageous application in the purification of a hydrofluoroalkane obtained by hydrofluorination, in particular by hydrofluorination of a hydrochloro(fluoro)carbon.

It should be understood that the different aspects of the invention can be combined with each other or with other purification treatments in order to optimise the benefits achieved by the process according to the invention. In a particular embodiment, the process according to the invention comprises 2, 3 or 4 purification steps for removing organic impurities, including at least one purification treatment according to the invention. In particular the combinations allow for effective reduction of chloro(fluoro) olefin content with very low losses of desired hydrofluoroalkane.

In the following paragraph describing combinations of purification treatments, the following abbreviations are used:
(a1) a treatment with chlorine according to the first variant of the first aspect of the process according to the invention;

(a2) a treatment with chlorine according to the second variant of the first aspect of the process according to the invention;
(a3) a treatment with chlorine according to the third variant of the first aspect of the process according to the invention;
(b) a reaction with hydrogen fluoride according to the second aspect of the process according to the invention;
(c) a distillation according to the third aspect of the process according to the invention;
(d) an extractive distillation according to the fourth aspect of the process according to the invention;
(e) an adsorption onto a solid adsorbent according to the fifth aspect of the process according to the invention;
(f) a reaction with a compound containing oxygen according to the sixth aspect of the process according to the invention;
(g) a gas-phase reaction according to the seventh aspect of the process according to the invention;
(h) a photochlorination using exclusively UV light of a wavelength >280 nm
(i) a photolysis in the absence of chlorine
(j) a reaction with fluorine
Suitable consecutive combinations include, amongst others, ("+" meaning "followed by")
(a3)+(a1), (a3)+(a2), (a3)+(c), (a3)+(e), (a3)+(h), (b)+(a1), (b)+(a2), (b)+(c), (b)+(e), (b)+(h), (c)+(a1), (c)+(a2), (c)+(c), (c)+(e), (c)+(h), (d)+(a1), (d)+(a2), (d)+(c), (d)+(e), (d)+(h), (f)+(a1), (f)+(a2), (f)+(c), (f)+(e), (f)+(h), (g)+(a1), (g)+(a2), (g)+(c), (g)+(e), (g)+(h), (i)+(a1), (i)+(a2), (i)+(c), (i)+(e), (j)+(a1), (j)+(a2), (j)+(c), (i)+(e), (i)+(h)+(c).
Combinations (a3)+(a1), (a3)+(a2), (a3)+(c), (a3)+(e), (a3)+(h), (c)+(a1), (c)+(a2), (c)+(c), (c)+(e), (c)+(h) (i)+(a1), (i)+(a2), (i)+(c), (i)+(e), (i)+(h)+(c) are preferred.
Combinations (a3)+(a1), (a3)+(a2), (a3)+(c), (a3)+(h), (c)+(a1), (c)+(a2), (c)+(c), (c)+(h), (i)+(h)+(c) are particularly preferred.
A variant of particularly preferred combinations includes (a3)+(a1)+(c), (3a)+(a2)+(c), (a3)+(c)+(c), (a3)+(h)+(c).
It is understood that the aforementioned combinations are particularly well suited for the purification of 1,1,1,3,3-pentafluorobutane.

The invention also relates to a purified hydrofluoroalkane, preferably chosen from 1,1,1,3,3-pentafluoropropane and 1,1,1,3,3-pentafluorobutane, which has a hydrofluoroalkene content of less than 30 ppm by weight and preferably less than 20 ppm. A hydrofluoroalkene content of less than 10 ppm is particularly preferred. When the hydrofluoroalkane is 1,1,1,3,3-pentafluorobutane, they are usually hydrofluoroalkenes of empirical formula $C_4F_4H_4$, mentioned above.

The examples which follow are intended to illustrate the present invention without, however, limiting its scope.

EXAMPLE 1

Chlorination Initiated by Electromagnetic Radiation, Comprising at Least One Fraction of Wavelengths Less than 280 nm 750 g of 1,1,1,3,3-pentafluorobutane (HFC-365mfc) containing 709 ppm by weight of olefinic impurities including 40 ppm of $C_4H_4F_4$ hydrofluoroalkenes and chlorine were introduced into a tank with a working volume of 0.7 l equipped with an immersion UV emitter of the type Heraeus TQ 150, the power of which was 150 W and the arc length of which was 44 mm. This low-pressure mercury vapour emitter has broadband emission in the range of UV rays above 190 nm. All the internal glassware between the emitter and the 1,1,1,3,3-pentafluorobutane was made of quartz. The molar ratio between the chlorine and the olefinic impurities was 1.6. The lamp was cooled so as to maintain the 1,1,1,3,3-pentafluorobutane at a temperature of 25° C. The medium was stirred by means of a magnetic bar. Samples were taken at regular intervals for analysis of the olefinic impurity content of the 1,1,1,3,3-pentafluorobutane by gas chromatography.

The table below shows the change in concentration of the olefins in the 1,1,1,3,3-pentafluorobutane which was observed after a given period of treatment with chlorine in the presence of UV light comprising a fraction of wavelengths less than 280 nm.

|  | 30 min | 1 h | 2 h |
| --- | --- | --- | --- |
| $C_4H_4F_4$ content (ppm/weight) | 9 | 5 | 0 |
| Total content of olefinic impurities (ppm/weight) | 83 | 18 | 0 |

EXAMPLE 2

Hydrofluorination

A reactor containing hydrogen fluoride and titanium tetrachloride was fed continuously with a 1,1,1,3,3-pentafluorobutane containing 5.8% by weight of two trifluorodichlorobutene isomers. The reactor was maintained at a temperature of about 130° C. with continuous stirring. The pressure was adjusted to 22 bar. The purified 1,1,1,3,3-pentafluorobutane was removed continuously in the gas phase. The content of the first trifluorodichlorobutene isomer in the purified 1,1,1,3,3-pentafluorobutane was 0.1% by weight. The content of the second trifluorodichlorobutene isomer in the purified 1,1,1,3,3-pentafluorobutane was 0.05% by weight.

EXAMPLE 3

Distillation with Removal from the Top of the Column

Distillation was carried out in a column packed with ⅝" "pall" rings. 1,1,1,3,3-Pentafluorobutane containing 94 ppm of 3 saturated chlorofluoro organic impurities containing 3 or 4 carbon atoms and 252 ppm of 2 (chloro)fluoro olefins containing 4 carbon atoms was fed in at the level of the column which corresponds to 43% of the number of theoretical plates. The pressure was 2 bar, the temperature was 60° C. and the degree of molar reflux was about 4. An amount of purified 1,1,1,3,3-pentafluorobutane corresponding to 84% of the feed was removed from the top of the column. This product still contained 6 ppm of a chlorofluoro saturated organic impurity containing 3 carbon atoms. The content of the other two saturated impurities was reduced below the 5 ppm detection limit. The content of the said 2 (chloro)fluoro olefins containing 4 carbon atoms in the purified 1,1,1,3,3-pentafluorobutane was reduced to below the 5 ppm detection limit.

EXAMPLE 4

Comparative

The distillation was carried out in the same apparatus as in Example 3. 1,1,1,3,3-Pentafluorobutane containing 170 ppm of 3 chlorofluoro saturated organic impurities containing 3 or 4 carbon atoms and 152 ppm of 2 chlorofluoro olefins containing 3 or 4 carbon atoms was fed into the level of the column which corresponds to 65% of the number of theoretical plates. The pressure was 2 bar, the temperature was 60° C. and the degree of molar reflux was about 25. An amount of 1,1,1,3,3-pentafluorobutane corresponding to 85% of the feed was removed from the bottom of the column. This product contained 170 ppm of the said 3 saturated organic impurities and 141 ppm of the said 2 chlorofluoro olefins containing 4 carbon atoms.

It appears that the third aspect of the process according to the invention allows a fast, efficient and complete purification of olefinic impurities, in particular of hydrofluoroalkenes, from the hydrofluoroalkane. No degradation of the hydrofluoroalkane HFC-365mfc was observed.

EXAMPLE 5

Reagent Containing Oxygen 1,1,1,3,3-Pentafluorobutane containing 3260 mg/kg of (chloro)fluoro olefinic impurities was mixed in the liquid phase with 96% sulphuric acid in a 1:1 1,1,1,3,3-pentafluorobutane/sulphuric acid ratio by volume. The mixture was stirred for 24 h at 40° C. After this period, the recovered 1,1,1,3,3-pentafluorobutane contained 140 ppm of (chloro)fluoro olefinic impurities.

EXAMPLE 6

Gas-phase Reaction 1,1,1,3,3-Pentafluorobutane with a purity of 99.86% by weight, containing 755 mg/kg of (chloro)fluoro olefinic impurities, was evaporated at 85° C. and fed continuously into a reactor, containing a catalyst consisting of 0.5% palladium on active charcoal. The reactor was also fed continuously with hydrogen. The molar ratio between the hydrogen and the 1,1,1,3,3-pentafluorobutane was $5.8 \times 10^{-3}$. The reaction temperature was 100° C. The gaseous effluents of the reaction were condensed with a water condenser at 5° C. and were analysed by GC. They consisted of 1,1,1,3,3-pentafluorobutane with a purity of 99.92% by weight, containing less than 5 mg/kg of (chloro)fluoro olefinic impurities. No degradation of the 1,1,1,3,3-pentafluorobutane was observed.

The invention claimed is:

1. Process for obtaining a hydrofluoroalkane comprising at least three carbon atoms, which is purified of organic impurities including (chloro)fluoro olefins, according to which the hydrofluoroalkane containing organic impurities is subjected to at least one purification treatment which allows an effective reduction of the content of the olefinic impurities chosen from
   (a) a treatment with chlorine in the presence of a initiator wherein said initiator is an electromagnetic radiation comprising at least one fraction of wavelengths less than 280 nm;
   (b) a reaction with hydrogen fluoride;
   (c) a distillation in which the purified hydrofluoroalkane is removed from the top of the distillation column or from the side and wherein the distillation column has at least 10 theoretical plates;
   (d) an extractive distillation which is carried out in the presence of at least one extractant selected from the group consisting of (hydro)chlorocarbon, (hydro)fluorocarbon, hydrochlorofluorocarbon, hydrocarbon, ketone, ether, ester, nitrile, hydrogen chloride and carbon dioxide;
   (f) a reaction with a compound containing oxygen wherein said compound containing oxygen is selected from the group is an oxygenated acid, an organic peroxide, an inorganic peroxide, a peroxide salt or a peracid;
   (g) a gas-phase reaction with a reagent capable of reacting with at least some of the organic impurities, with the exception of a reaction with elemental chlorine wherein said reagent is hydrogen, hydrogen chloride or hydrogen fluoride; and
   (h) a gas-phase reaction with a reagent capable of reacting with at least some of the organic impurities, with the exception of a reaction with elemental chlorine and wherein the reaction is a catalytic hydrogenation.

2. The process according to claim 1, wherein said initiator is an electromagnetic radiation comprising at least one fraction of wavelengths less than 280 nm.

3. The process according to claim 2, wherein said energy of the fraction of wavelengths less than 280 nm is at least 10% of the total energy of the electromagnetic radiation.

4. The process according to claim 2, in which the molar ratio between the chlorine and the sum of the olefinic impurities present is from 1 to 10.

5. The process according to claim 2, in which the molar ratio between the chlorine and the sum of the olefinic impurities present is less than 1.

6. The process according to claim 1, in which the hydrofluoroalkane containing organic impurities is subjected to a reaction with hydrogen fluoride.

7. The process according to claim 6, in which the reaction with hydrogen fluoride is carried out in the presence of a fluorination catalyst, and the reaction with hydrogen fluoride is carried out in the liquid phase.

8. The process according to claim 7, wherein said fluorination catalyst is a compound containing a metal selected from the group consisting of group IIIa, IVa, IVb, Va, Vb and VIb of the periodic table of elements.

9. The process according to claim 6, in which a molar ratio between the hydrogen fluoride and the olefinic impurities of not more than 3 is maintained.

10. The process according to claim 1, in which the hydrofluoroalkane containing organic impurities is subjected to a distillation and the purified hydrofluoroalkane is removed from the top of the distillation column or from the side and wherein the distillation column has at least 10 theoretical plates.

11. The process according to claim 10, in which the temperature at which the distillation is carried out corresponds approximately to the boiling point of the hydrofluoroalkane at the chosen pressure.

12. The process according to claim 6, in which the feed of hydrofluoroalkane containing organic impurities is carried out at a level of from 5% to 50% of the number of theoretical plates of the column.

13. The process according to claim 6, in which the side removal is carried out at the level which corresponds to from 50% to 80% of the total number of theoretical plates of the distillation.

14. The process according to claim 1, in which the extractive distillation is carried out in the presence of at least one extractant selected from the group consisting of (hydro)chlorocarbon, (hydro)fluorocarbon, hydrochlorofluorocarbon, hydrocarbon, ketone, ether, ester, nitrile, hydrogen chloride and carbon dioxide.

15. The process according to claim 1, in which the compound containing oxygen is selected from the group consisting of hydrogen peroxide, peracetic acid, potassium permanganate, sulphuric acid, and sulphur trioxide.

16. Process for obtaining a hydrofluoroalkane comprising at least three carbon atoms, which is purified of organic impurities including (chloro)fluoro olefins, according to which the hydrofluoroalkane containing organic impurities are subjected to at least 2, 3 or 4 purification treatments for removing organic impurities wherein said purification treatment chosen from
- (a) a treatment with chlorine in the presence of a initiator,
- (b) a reaction with hydrogen fluoride,
- (c) a distillation in which the purified hydrofluoroalkane is removed from the top of the distillation column or from the side,
- (d) an extractive distillation,
- (e) an adsorption onto a solid adsorbent,
- (f) a reaction with a compound containing oxygen, and
- (g) a gas-phase reaction with a reagent capable of reacting with at least some of the organic impurities, with the exception of a reaction with elemental chlorine.

17. Purified hydrofluoroalkane selected from the group consisting of 1,1,1,3,3-pentafluoropropane and 1,1,1,3,3-pentafluorobutane, which has a hydrofluoroalkene content of less than 30 ppm by weight.

18. The process according to claim 1, wherein the purification treatment is the gas-phase reaction with a reagent capable of reacting with at least some of the organic impurities, with the exception of a reaction with elemental chlorine wherein said reagent is hydrogen, hydrogen chloride or hydrogen fluoride.

19. A process for obtaining a hydrofluoroalkane comprising at least three carbon atoms, which is purified of organic impurities including (chloro)fluoro olefins, according to which the hydrofluoroalkane containing organic impurities is subjected to at least one purification treatment that is a gas-phase reaction with a reagent capable of reacting with at least some of the organic impurities, with the exception of a reaction with elemental chlorine wherein said reagent contains hydrogen.

20. The process as claimed in claim 19, wherein said reagent containing hydrogen is hydrogen chloride or hydrogen fluoride.

* * * * *